United States Patent [19]

Pittaro

[11] Patent Number: 5,113,706

[45] Date of Patent: May 19, 1992

[54] ULTRASOUND SYSTEM WITH DYNAMIC TRANSMIT FOCUS

[75] Inventor: Richard J. Pittaro, San Carlos, Calif.

[73] Assignee: Hewlett-Packard Company, Palo Alto, Calif.

[21] Appl. No.: 548,162

[22] Filed: Jul. 3, 1990

[51] Int. Cl.[5] .......................... G01N 9/24; A61B 8/00
[52] U.S. Cl. ................................... 73/626; 128/661.01
[58] Field of Search ................. 73/602, 626, 625, 627, 73/620, 619, 623; 128/661.01, 660.07, 660.08

[56] References Cited

U.S. PATENT DOCUMENTS

| | | | |
|---|---|---|---|
| 4,227,417 | 10/1980 | Glenn | 73/625 |
| 4,290,310 | 9/1981 | Anderson | 73/626 |
| 4,870,971 | 10/1989 | Russell et al. | 128/661.01 |
| 4,974,211 | 11/1990 | Corl | 73/626 |
| 5,014,712 | 5/1991 | O'Donnell | 128/661.01 |

OTHER PUBLICATIONS

"Quadrature Sampling For Phased Array Application", by J. E. Powers, D. J. Phillips, M. Brandestini, R. Ferrara, and D. W. Baker, Center for Bioengineering, University of Washington, Seattle Washington (date unknown).

Primary Examiner—Hezron E. Williams
Assistant Examiner—Louis M. Arana

[57] ABSTRACT

An ultrasound system steps focus and power through a series of focal zones to provide real-time seamless images with a range exceeding the depth of field of the employed ultrasound transducer. The information required for the focus and power functions are stored in memories which are read out by a zone sequencer. The data is stored in registers in the drive circuitry so that no time is lost in generating succeeding power bursts. Echoes are received from successive zones at a given steering position rather than at successive steering positions of a given zone. Provision is also made for adapting time-varying gain functions applied at a receiver as a function of zone to optimize contrast uniformity and minimize contrast discontinuities. The zone sequencer controls the input of processed echo signals into a video buffer, gating out unwanted information and splicing echo signal segments from successive zones into continuous sector lines for display on a monitor. Echoes are gathered from all zones at each steering position rather than at all steering positions for each zone so as to minimize temporal discontinuities in the constructed image.

10 Claims, 3 Drawing Sheets

ULTRASOUND SYSTEM WITH DYNAMIC TRANSMIT FOCUS

BACKGROUND OF THE INVENTION

The present invention relates to ultrasound imaging and, more particularly, to ultrasound imaging using phased-array transducers. A major objective of the present invention is to provide for improved real-time ultrasonic imaging where the image depth exceeds the depth of field of the ultrasonic transducer.

Ultrasound imaging is widely used for non-invasive investigation of a subject. Medical applications include cardiac monitoring and fetal monitoring. A typical ultrasound imaging system comprises a base module and a probe. The base module generates an electrical pulse burst which is converted to an ultrasound acoustic wavefront by a transducer in the probe. When the probe is pressed against a subject, the acostic wavefront is transmitted into the body and is reflected to different degrees wherever it encounters a change in ultrasonic impedance (the product of density and propagation velocity) at tissue or bone boundaries. Echoes from different boundaries reach the transducer at different times depending on the distance of the respective boundaries from the transducer. The transducer converts the echoes into time-varying electrical signals which are processed to form a video presentation of the subject being imaged.

Fixed focus ultrasound systems are known which employ spherical or parabolic transducers. Applying an electrical pulse to such such a transducer generates an ultrasound wavefront which converges at the transducer's focal point. The focal range for fixed-transducer ultrasound systems is its depth of field. The sensitivity, i.e., ability to detect relatively weak echoes, of such a system is related to the aperture area available for detecting these echoes. Greater sensitivity can be obtained by using a larger aperture.

As in optical systems, larger apertures are associated with greater energy gathering ability but shallower focal ranges. Thus, greater sensitivity can be achieved at the expense of focal range. Greater sensitivity can also be obtained by increasing the power transmitted into a subject of interest; however, the transmit power is constrained by subject welfare considerations as codified in regulations of the Food and Drug Administration (FDA). Thus, in practice, for fixed focus systems, there is a tradeoff between sensitivity and focal range.

A variable-focus transducer can provide a focal range greater than its instantaneous depth of field. Thus, higher sensitivity can be obtained along with a greater focal range. While mechanical deformation of a transducer to vary its focal depth is conceivable, it is not practical. An "electronic deformation" is accomplished in a phased-array transducer, a development derived from radar technology. A phased-array transducer comprises multiple transducer elements in one of several spatial configurations. By introducing variable relative delays between the electrical channels associated with respective transducer elements, the focal depth of the array can be adjusted.

There are three basic types of phased-array transducers: planar, linear and annular. Planar arrays comprise a two-dimensional array of "point source" transducer elements. Linear arrays comprise a one-dimensional array of linearly-extending "line source" transducer elements. Annular arrays comprise a radially extending array of circular transducer elements, i.e., coaxial rings.

All three array types provide electronic focusing. Planar and linear arrays can be steered electronically, while annular arrays are steered mechanically. Planar arrays provide full electronic control of steering and focusing, as well as the ability to resolve in three dimensions. They have not been used widely due to the large number of transducer elements and corresponding signal processing channels required to achieve a given resolution. For example, a planar array which can focus in azimuth would require 500 to 1,000 transducer elements and channels to achieve the resolution attainable by a twelve-element annular array. To steer in azimuth would require 5,000 to 10,000 transducer elements. Linear arrays provide electronic steering and focusing, but fail to resolve in the azimuthal direction. This disadvantage limits their usefulness for many applications.

Annular arrays resolve in three dimensions and have relatively modest signal processing requirements. Mechanical steering can be slower than electronic steering. Typically, an annular array is constantly wobbled fast enough so that a human operator does not perceive a significant delay in the acquisition of image data from two different angular positions. Mechanical steering introduces some limitations in that steering positions are acquired serially rather than by direct "random" access, as is provided by electronically steered arrays. Another disadvantage is that the transducer array is moving between the time a wavefront is transmitted and the time the last echo of interest is received. Complex signal processing can be required if it is deemed necessary to remove the resulting distortion. In practice, annular arrays provide cost effective ultrasonic imaging.

In an annular array transducer system, as in other phased array systems, a burst comprising parallel trains of one or more electrical pulses is generated. Each pulse train is directed to a respective transducer ring on a respective transmit channel. Each transducer ring receives its respective pulse train, which it converts to an ultrasound pulse. The ultrasound pulses generated at the different transducer rings combine to define an ultrasound wavefront. If the elements of the array collectively define a spherical or parabolic shape, the wavefront can converge at the geometric focal point of the array. An image obtained using such a wavefront will be sharpest at the focal point and increasingly out of focus at shallower and deeper positions along the same steering axis. For a given application, "acceptable" focus is obtained within a geometric depth of field, which includes the geometric focal point.

A focal point other than the geometric focal point is achieved by introducing relative delays in the pulse trains. Relatively longer delays applied to the inner transducer rings result in a wavefront which converges nearer to the array, i.e., a shallower focal point is effected. Shorter delays applied to the inner transducer rings effect a greater focal depth. The delays are selected to compensate for the path differences between respective transducer rings and a targeted focal point. Thus, focal depth can be varied by adjusting the relative delays between inner and outer transducer rings.

Relative delays can be introduced both in the transmit channels and in the receive channels. Generally, the focal point for reception should be the same as the focal point for transmission. This is qualified by the availability of dynamic receive focus, which has no direct counterpart for transmission. The echoes resulting from a single transmit burst are received chronologically according to the distance between the respective boundaries generating the echos from the transducer array. A receiver implementing dynamic receive focus, adjusts the relative channel delays so that the instantaneous focal point tracks the position from which echoes are received at that instant. Dynamic receive focus optimizes focus through the reception of the echoes from each burst.

Dynamic receive focus takes advantage of the fact that burst's energy is distributed in space and time before echo reception. There is no comparable time distribution of energy at the time the pulse is transmitted. The duration of a pulse burst is too short to permit viable changes of focus during a pulse burst. Accordingly, the advantages provided by dynamic receive focus have not been transferred to the transmitter. Therefore, the instantaneous focal range of an ultrasound system remains limited by the transducer's instantaneous depth of field.

Multiple steering sweeps can be used to view an area deeper than the depth of field. The transducer is rotated over a desired steering range while the transmitter selects delays corresponding to a first focal depth. This results in an image which includes a band (defined by the depth of field) of acceptable focus. A second steering sweep provides a second band of acceptable focus. These bands can be juxtaposed to provide a range of acceptable focus greater than the transducer's depth of field.

There are two problems with images obtained by juxtaposing successively acquired bands of acceptable focus: seams in the image and the lack of real-time feel. In most medical applications, the object of interest, e.g., a fetus or heart, is moving. Since an ultrasound image is acquired over time, some object motion occurs during imaging. As long as neighboring points represent neighboring instants, the collective image remains coherent and useful. However, when bands of acceptable focus are juxtaposed neighboring points on either side of the boundary between the bands represent the object at significantly different times. The band boundary becomes a visual time warp and impairs interpretation of the image.

An ultrasound operator generally moves the ultrasound probe about to view different areas within a subject. The movement can serve to locate an object requiring further study or it can serve to track an extended feature such as an artery. Ergonomic studies have shown that an ultrasound image must be updated within a certain time for the operator to feel as though the imaging is occurring in real time. If the imaging updating is slower than about 7–11 Hz, the eye-probe coordination of the operator is broken. This can impair investigation, and this impairment is exacerbated by the operation aggravation which usually accompanies the loss of real-time feel.

If two or more steering cycles are required to complete an image, there is a challenge in obtaining the multiple sweeps within the limit required for ergonomic updating. The steering speed is limited by the need to wait for echoes before firing pulses for the next steering position. Mechanical steering inevitably imposes some time loss between steering cycles.

Planar arrays are not restricted by mechanical steering but are faced with the delays in processing many times the information handled by annular arrays. Planar arrays must also address the problem of time discontinuities at band boundaries. All ultrasound systems are restricted by the time of flight of ultrasound in the body.

What is needed is an ultrasound system which provides full focus images of areas of depth greater than the instantaneous depth of field of the transducer aperture. This would permit high sensitivity and extended focal ranges to be combined more advantageously. The full focus images should be relatively free of temporal discontinuities. Furthermore, the imaging system should permit full range, full focus imaging within the ergonomic limits required for real time feel.

SUMMARY OF THE INVENTION

In accordance with the present invention, an ultrasound system employs a transmitter section including a zone sequencer for cycling through a series of focal zones at each transducer steering position, and a power modulator which adjusts deliverable power density as a function of the current zone. Signals from successive bursts in a cycle are spliced together after reception to yield a full range image without temporal discontinuities. In effect, dynamic transmit focus with corresponding gain compensation is implemented over a series of pluse bursts.

In practice, a diagnostician can input a selected image depth range into a controller for the ultrasound system. The system preferably employs a phased-array electroacoustic transducer with a large aperture for high sensitivity; thus, a practical selected focal range typically exceeds the depth of field associated with the aperture. A zone sequencer divides this selected range into a series of focal zones, each of which embodies a depth range within the depth-of-field constraints of the aperture. In other words, the transducer is suited for imaging an entire zone with acceptable focus. Preferably, the zones are ordered by increasing depth.

The transmit section includes a burst generator, which generates parallel pulse trains. Each pulse train comprises one or more electrical pulses and is directed to a respective transducer element of the phased-array transducer. The relative delays between the pulse trains of a burst determine the focal point of the wavefront resulting from the burst. The zone sequencer causes delay circuitry to step the focal points of successive wavefronts through successive zones. Each focal point is selected to be located within a respective zone so that the depth of field about the focal point extends to the near and far zone boundaries. The delays can be adjusted rapidly during a series of pulses by reading out preprogrammed delays from a focus ROM lookup table.

The zone sequencer also provides current zone information to the power modulation circuitry. Safety guidelines dictate that delivered ultrasound power density be maintained within established maxima. However, for a given transmit power, delivered power density varies with focal depth due to attenuation of acoustic signals in a subject. Therefore, transmission power can be increased with focal depth while meeting safety requirements. In practice, transmission power must be increased with focal depth to compensate for attenuation and beam-spreading. A transmit power meeting power requirements for lesser depths is not sufficient for generating images at much greater depths. Accordingly, wide range imaging is enhanced by stepping up transmit power as zone depth is increased.

Transmit power can be varied in different ways: 1) by controlling the amplitude of pulses; 2) by controlling the duration of pulses; 3) by controlling the number of pulses in a pulse train, effectively controlling burst duration; and 4) by selectively enabling and disabling transducer elements, effectively changing the number of pulse trains. The present invention provides for modulating any one of these parameters or any combination of these parameters by zone.

The present invention provides for varying burst frequency by zone. The burst frequency is the fundamental frequency of its pulse trains and determines the fundamental frequency of the generated acoustic wavefronts. Acoustic wavefronts with higher frequencies attenuate more rapidly than those with lower frequencies. Hence, transmit power calculations can take frequency into account when determining the transmit power required to achieve a given delivered power density to a focal point. Similarly, soft focus techniques can affect the power density delivered by a wavefront having a given transmit power. Advantageously, pulses can be generated as square waves, in which case pulse duration and burst frequency are closely related parameters.

The foregoing system can cycle through a series of bursts in which successive bursts are characterized by increasing focal depth and increasing power. At the end of a cycle, the series can be repeated for a new steering position. Cycling continues until the total steering angle range is completely swept.

The echoes resulting from the burst cycles can be processed in a manner similar to those produced by systems which steer through one zone at a time. The echo signals are received, gain adjusted, optionally digitized, preferably subjected to relative delays, combined, and converted to video for display. At some point in the receive chain, the echoes signals from successive zones must be spliced to provide an integrated video image spanning multiple zones. The splicing can be effected by gating a video buffer using a "zone active" signal and resetting the zone buffer in response to a "cycle end" signal transmitted by the zone sequencer. Optionally, a time-varying gain signal can be varied as a function of zone to compensate for the different amounts of power transmitted to successive zones, thus smoothing the representation of zone transitions in the displayed image.

To provide for real time feel, the proper delays and power adjustments must be made without incurring significant delays. In particular, a power supply must be able to transition between successive pulse power levels at the burst firing rate. The pulse amplitudes can be computed at the beginning of a steering sweep and stored in an addressable memory. The zone sequencer reads the power level of a succeeding burst out of the memory by the time a preceding burst is fired. This value is admitted to a power supply register just after the first burst is completed. The power supply then has time, until all echoes of interest have been received, to achieve the power level required of the next burst. Focus and other stepped parameters can also be adjusted rapidly with proper synchronization as the zone sequencer successively addresses respective memories, and the values read out are stored in registers of components dedicated for implementing the parameters.

The present invention thus provides for dynamic transmit focus with a corresponding time-gain fuction. The transmit dynamics effect focus and power sweeps over a series of bursts. This contrasts with prior art receive dynamics in which focus and power sweeps occur for each burst. Thus, the present invention provides for transmit and receive dynamics on two different scales. Transmit focus and power are stepped over the entire multi-zone focal range of interest. Receive focus and gain are swept over each transmit zone, and thus, generally, swept several times during one transmit sweep.

Just as the use of phased arrays overcame the limitations of transducers with fixed focal lengths, the present invention overcomes the limitations of phased-array transducers with fixed apertures. Previously, designers had to comprise between large apertures for maximum sensitivity and small apertures for greater depth of field. The present invention permits a designer to select an aperture for the desired sensitivity and splice zones to construct the desired focal range.

The present invention offers particular advantages in the context of annular phased arrays. Without dynamic transmit focus, a diagnostician would have to sweep an annular array successively through each of the several zones spanning a desired focal range. The steering sweep speed is limited by the mechanics of the steering apparatus. Considerable delay is required to complete the multiple steering sweeps required to assemble images from multiple zones. If the subject matter is moving, there will be discontinuities at the zone boundaries. The zone splicing provided by the present invention minimizes such discontinuities and requires only one mechanical steering sweep to complete an image having a desired focal range. These and other features and advantages of the present invention are apparent from the description below with reference to the following drawings.

DESCRIPTION OF THE PREFERRED EMBODIMENTS

Figures 1, 2:
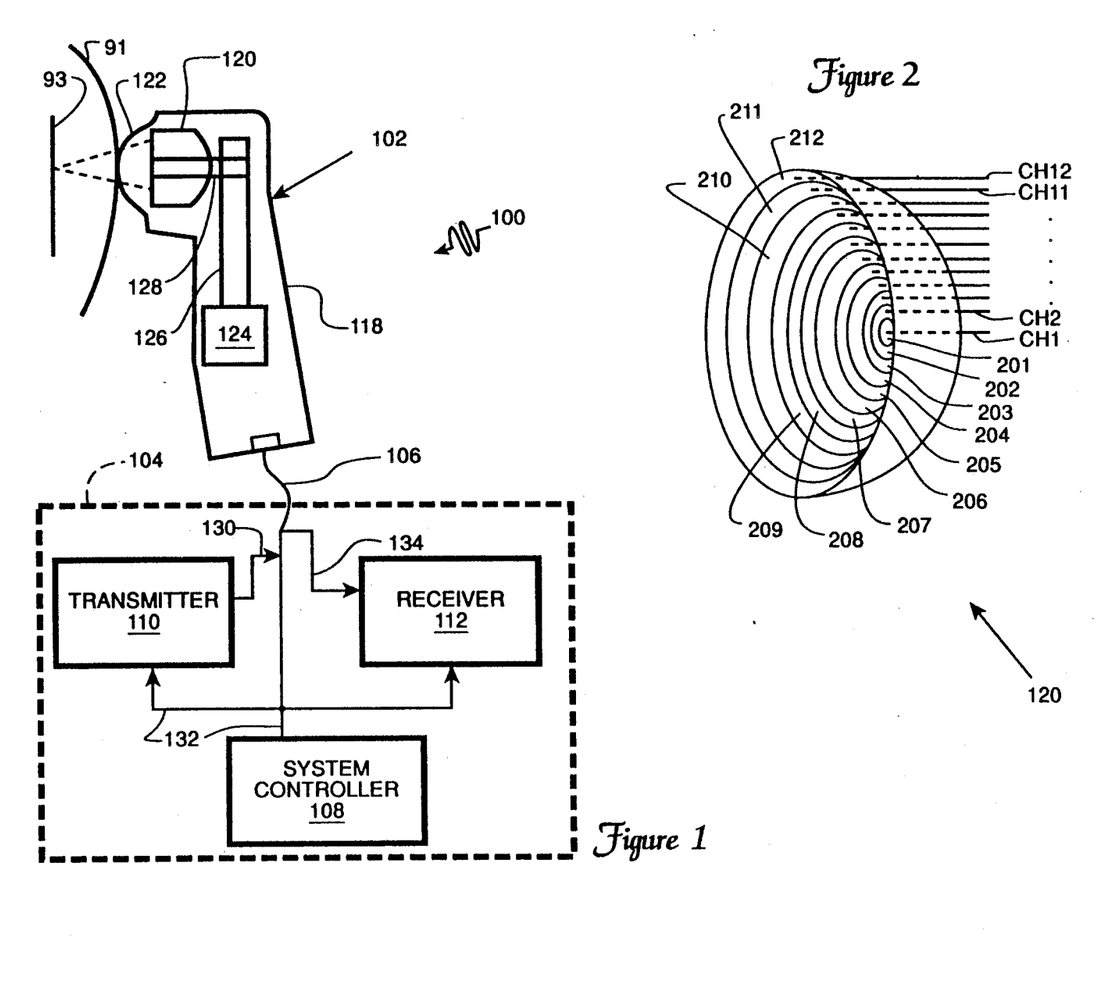
FIG. 1 is a schematic of an ultrasound system in accordance with the present invention.
FIG. 2 is a schematic perspective view of a transducer incorporated in the ultrasound system of FIG. 1.

An ultrasound system 100 includes a probe 102 and a base unit 104 which are connected via a cable 106, as shown in FIG. 1. Probe 102 is shown disposed against a subject body 91 having an internal impedance boundary 93, such as tissue, at which ultrasound energy can be reflected.

Base unit 104 comprises a system controller 108, a transmitter 110, and a receiver 112. Probe 102 includes a probe housing 118, a transducer 120, a probe window 122, a motor 124, a motor shaft 126, and a drive belt 128. System controller 108 is coupled to transmitter 110 and receiver 112 via a control bus 132. Transmitter 110 transmits power bursts to transducer 120 via transmit bus 130, while receiver 112 receives echo signals resulting from these bursts from transducer 120 via receive bus 134. Transducer 120 includes twelve concentrically arranged annular transducer elements 201-212 configured to conform to a section of a sphere, as indicated in FIG. 2. Each transducer element 201-212 defines a respective signal channel CH1-CH12.

Figure 3:
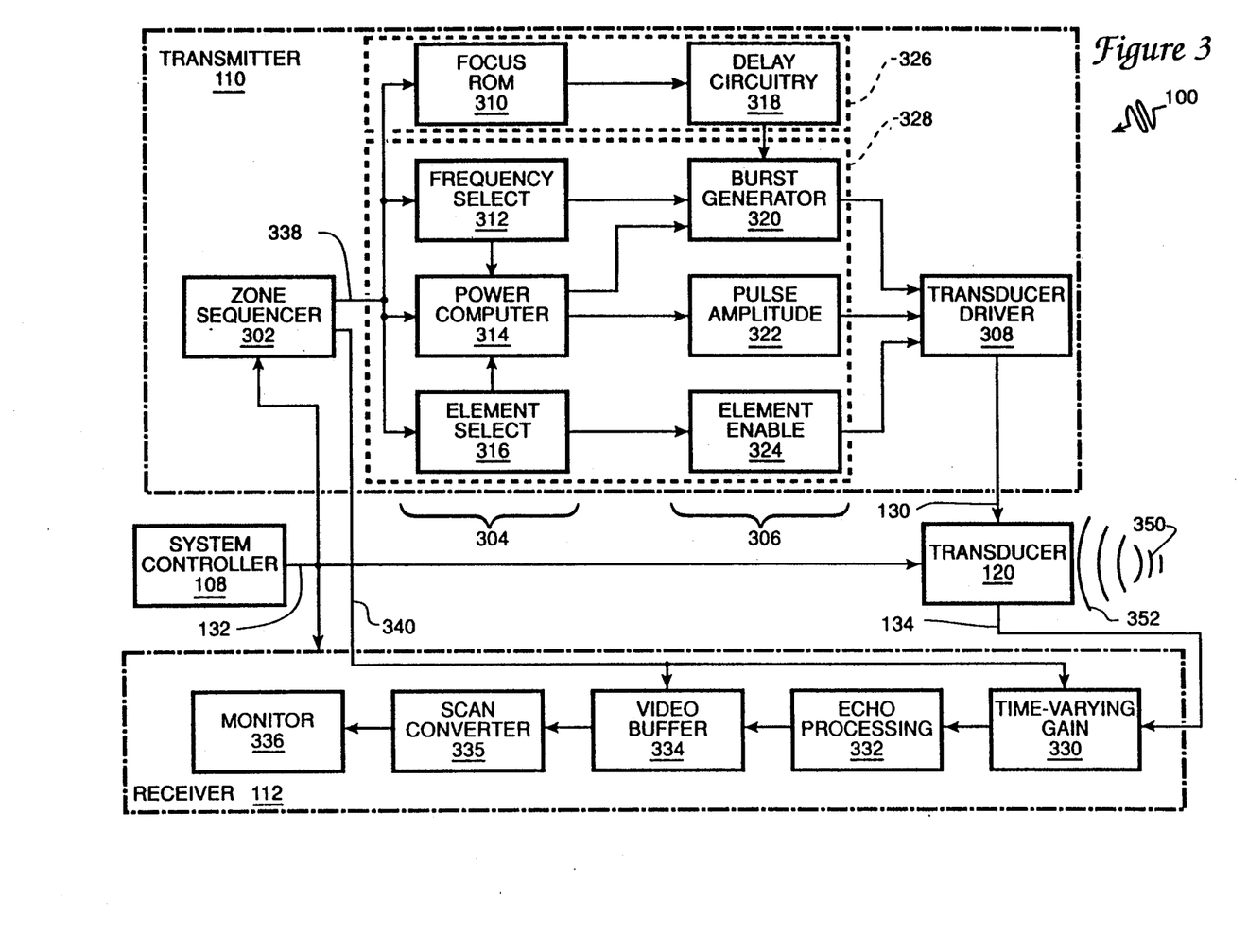
FIG. 3 is a block diagram of the ultrasound system of FIG. 1.

Transmitter 110 comprises a zone sequencer 302, a transmit data generator 304, a transmit drive controller 306, and a transducer driver 308 as shown in FIG. 3. Zone sequencer 302 selects a series of contiguous zones which span a selected target depth range. Transmit data generator 304 includes a focus ROM 310, a frequency select section 312, a transmit power computer 314, and an active element select 316. These components respectively determine delay, frequency, pulse amplitude, and the number of transducer elements activated; all of these parameters are calculated as a function of the zone references issued by zone sequencer 302.

Transmitter drive section 306 includes focus delay circuitry 318, a burst generator 320, a pulse amplitude controller 322, and element enable circuitry 324. Focus ROM 310 and delay circuitry 318 constitute a focus section 326 that serves to define the focal depth of a burst generated by transducer driver 308. Frequency select section 312, burst generator 320, power computer 314, pulse amplitude controller 322, element select section 316 and element enable controller 324 collectively constitute a power section 328 that determines the transmit power for each burst.

Transducer driver 308 is the source of the power bursts that are converted to acoustic wavefronts by transducer 120. The components of transmitter drive controller 306 configure the burst according to the data from transmit data generator 304. Burst generator 320 is coupled to frequency select section 312 which effectively determines pulse duration and burst frequency, which is the pulse rate of the trains. Burst generator 320 is also coupled to power computer 314 which can compute pulse count. Pulse count and pulse amplitude both contribute to pulse power; power computer 314 can be programmed to covary these parameters as called for by particular applications.

Receiver 112 includes a time-varying gain section 330, an echo processing section 332, a video buffer 334, a scan converter 335, and a monitor 336. Gain section 330 includes twelve time-variable amplifiers, one for each transducer elements 201-212. The gains of these amplifiers are increased while echoes from a burst are received to compensate for the greater attenuation to which the later, and therefore deeper, echoes are subject. Echo processing section 332 introduces relative delays in concurrent echo signals and combines the as-delayed echo signals to yield a video signal segment. Video buffer 334 gathers successive video signal segments of a burst cycle and assembles them into a radial sector line for display on monitor 336. Video buffer 334 also receives zone active signals and cycle end signals from zone sequencer 302 to effect the splicing of echo signal segments. Scan converter 335 converts sector data to raster data for display on monitor 336.

Figure 4:
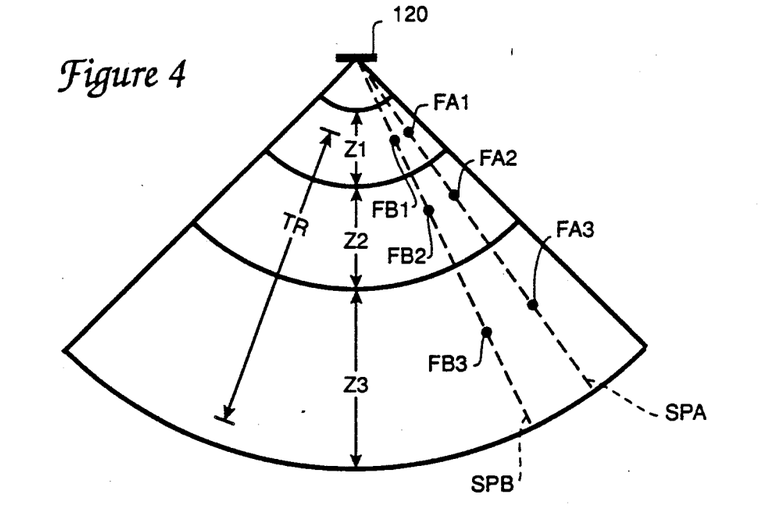
FIG. 4 is a schematic of the field of view of the ultrasound system of FIG. 1.

Transmitter 110 is designed to generate images while sweeping through a steering range such as the one illustrated in FIG. 4. During each steering sweep, transmitter 110 transmits burst cycles, each cycle corresponding to a respective angular steering position SPA, SPB, etc. Each steering position is actually a small arc since motor 124, FIG. 1, rotates transducer 120 continuously. Each burst cycle includes a series of bursts; each burst in a sweep generates a wavefront which converges at its respective focal point. The position of a burst in a burst cycle determines the focal depth of its respective focal point. The number of bursts in a burst cycle is the number of zones used to cover the target focal range. Thus, for a three-zone division, each burst cycle has three bursts. For example, the burst cycle BA1, BA2, BA3 for steering position SPA generates three wavefronts which converge successively and respectively at focal points FA1, FA2, and FA3; and the wavefronts for steering position SPB converge at focal points FB1, FB2, and FB3.

Each burst includes multiple pulse trains. Each pulse train includes one or more electrical pulses. The number of pulse trains is equal to the number of "enabled" transducer elements. Thus, there are a maximum of twelve pulse trains in a pulse burst of system 100. The trains of a pulse are replicas of each other in that they all contain the same number of pulses, and the pulses share common durations and amplitudes. A burst's pulse trains are concurrent to generate a common wavefront, but can be delayed relative to each other by variable amounts to control the focal depth of the resulting wavefront.

The relative delays of the pulse trains are varied in response to zone reference signals issued by zone sequencer 302. The zone reference signals address focus ROM 310 which contains data representing relative delays. The contents of each focus ROM address specify the set of delays to be applied to the pulse trains of a burst so that the generated wavefront converges within the zone specified by zone sequencer 302.

The data read out by a zone address is stored temporarily in a register of delay circuitry 318, which uses the stored data to control delays of twelve timing signals generated by burst generator 320. These timing signals act as switches which couple and decouple a voltage from pulse amplitude controller 322, which includes a programmable power supply, to the output of transducer driver 308. From another point of view, transducer driver 308 serves to amplify the timing signals from burst generator 320 according to a gain set by pulse amplitude controller 322.

The readout of focus data from focus ROM 310 is pipelined so that a succeeding burst can be generated as soon as the echoes of interest from the preceding burst have been received. Zone sequencer 302 can address the delay data for a succeeding burst before a preceding burst is triggered. As soon as the preceding burst has been transmitted, the delay data can be stored in the temporary register of delay circuitry 318. By the time the last echo of interest from the preceding burst should have been received, the data in the register is applied to burst generator 318. Zone sequencer 302 then triggers burst generator 320 to initiate the succeeding burst. Zone sequencer 302 is coupled to all components of transmit data generator 304 and transmitter drive controller 306 through a timing bus which is not separately shown.

The power of bursts in a cycle is increased with increasing focal depth to compensate for the increased attenuation and increased beam spread, to which echo signals from the deeper zones are subjected. For example, the power of burst BA2, FIG. 5, which corresponds to focal point FA2, FIG. 4, of zone Z2 is greater than the power of burst BA1 which converges in zone Z1. Likewise, the power of burst BA3 is greater than that of BA2. The power of burst BB1, which converges at focal point FB1 of zone Z1, is the same as that of burst BA1; likewise, burst BB2 has the same power as burst BA2, etc.

Burst power can be varied in several ways. The average amplitude of pulses in a burst can be varied. Generally, all pulses in a burst have the same amplitude, so changing average amplitude is the same as changing the common amplitude of the pulses. Similarly, average pulse duration can be increased to increase burst power. The common, or average, number of pulses in the pulse trains of a burst can be increased to increase power. Power can also be varied by changing the number of pulse trains. As indicated above, the number of pulse trains is determined by the number of transducer elements enabled.

Changing burst power is the primary method of determining delivered power density. However, the power delivered by two bursts of equal power to a common focal point can be different if the bursts are characterized by different fundamental frequencies. Generally, higher frequency wavefronts are attenuated more rapidly than lower frequency ultrasound components; accordingly, delivered power can be increased by decreasing frequency.

All of these methods for controlling delivered power intensity can be implemented by transmit drive circuitry 306 as dictated by transmit data generator 304. Transmit data generator 304 is programmable from system controller 108 via zone sequencer 302. Frequency select section 312 has a random access memory (RAM) which can be preloaded with a function by which frequency is to vary by zone. Element select section 316 has RAM which can be loaded with a function by which the number of transducer elements 201-212 enabled varies by zone. For example, if frequency select section 312 is programmed to decrease frequency, and thus increase burst duration, with increasing zone depth, power computer 314 will increase pulse amplitude to a lesser degree than if frequency is held constant. Likewise, changes in pulse amplitude with zone are affected by whether or not the number of transducer elements enabled or the number of pulses per train is varied.

Power computer 314 has access to the RAM of frequency select section 312 and of element selection 316 so that it can use the data on burst frequency, which corresponds to burst duration, and the number of pulse trains to determine the pulse amplitude and pulse count required to optimize burst power for each zone. Power computer 314 includes an instruction RAM which can be loaded with instructions which determine how pulse amplitude and pulse count are to covary by zone, frequency and element select. Power computer 314 also includes a data RAM so that amplitude and count determinations can be predetermined. The data RAM can then be addressed by sequencer 302 as bursts are generated so that computation time does not delay burst firing. In an alternative embodiment, zone sequencer 302 communicates frequency and element select data directly to the power computer 314; while the frequency select 312 and element select 316 do not communicate directly with the power computer 314.

Power determinations are pipelined in a manner similar to delay determinations. Sequencer 302 addresses a pulse amplitude and count for a succeeding burst before the preceding burst is transmitted. Once the preceding burst is fired, the addressed amplitude data is entered into a register of a programmable power supply of pulse amplitude controller 322. The address count data can be entered into a register of burst generator 320, setting the pulse count of the next timing signal. The amplitude data in the power supply register causes the power supply to ramp to the represented voltage level. This voltage is the peak voltage of the pulses, which are actually square waves with the timings set by burst generator 320. The power supply has the full inter-burst interval to stabilize at the voltage required by the succeeding burst.

The contents of each element enable RAM address is a twelve-bit word indicating which elements are to be enabled for each zone. The enable data for the current zone is stored in a register of element enable controller 324. The contents of this register enable and disable the twelve channels CH1-CH12 on bus 130 between transducer driver 308 and transducer 120. Pulse trains are transmitted only on enabled channels so that element select section 316 determines the number of pulse trains, which is proportional to the transmit power of a given burst. The element select RAM has twenty address locations, corresponding to the maximum number of zones provided by ultrasound system 100. The contents of the element select RAM are provided to power computer 314 for the pre-computation of pulse amplitude.

A default enable sequence is installed upon initialization. The default sequence can be overwritten via zone sequencer 302 and system controller 108. When fewer than all elements are enabled, the outer elements, e.g., 212, are preferentially disabled. Disabling outer elements changes the effective transmit aperture of transducer 120. Reducing the effective transmit aperture increases depth of field. Disabling more of the outer transducer elements at shallower focal zones offsets the loss of depth of field that would otherwise occur closer to transducer 120. Disabling elements also reduces transmit power, which must be reduced at shallower focal depths anyway. In the default sequence, only the inner four transducer elements are enabled for zone Z1, the inner eight for zone Z2, and all twelve for zone Z3.

Frequency select section 312 is similar to element select section 316. A frequency select RAM can be programmed so that frequency can be stepped on a per-zone basis. Normally, the frequency is constant for all zones. When frequency is varied, it is generally decreased for more distant zones. The higher frequencies provide greater resolution at shallower depths of focus. The lower frequencies provide stronger echo signals for the deeper zones due to lesser attenuation. The contents of the frequency select RAM are provided to power computer 314 for the pre-computation of pulse amplitudes. The frequency select RAM is read in real time, its contents being sequentially provided to a register of burst generator 320.

Transmitter 110 thus generates burst cycles along transmit bus 130, which are converted to wavefronts 350 by transducer 120, as shown in FIG. 3. Wavefront echoes 352 are converted to electrical echo signals by transducer 120 and conveyed to receiver 112 along twelve-channel receive bus 134. Each burst produces a transmitting wavefront, which produces an acoustic echo, which yields up to twelve echo signal segments. The concurrent echo signal segments resulting from a single burst constitute a respective echo signal set.

Time-varying gain section 330 includes a band of twelve time-varying gain amplifiers corresponding to transducer elements 201-212. The gain applied to each echo signal segment is increased over time to compensate for the increased attenuation to which echo signals from deeper boundaries in a zone are subjected. Each time-varying gain amplifier can apply a time-varying gain to each echo signal segment received by its respective transducer element. Different time-varying gain functions can be applied concurrently by the different amplifiers. The different gains can be used to weight the echo signal segments from the different transducer elements to apodize the echo so that side lobes are reduced. However, in system 100 acoustic apodization is implemented by probe window 122, FIG. 1, so that electrical apodization at gain section 330 is not necessarily required.

Figure 6:
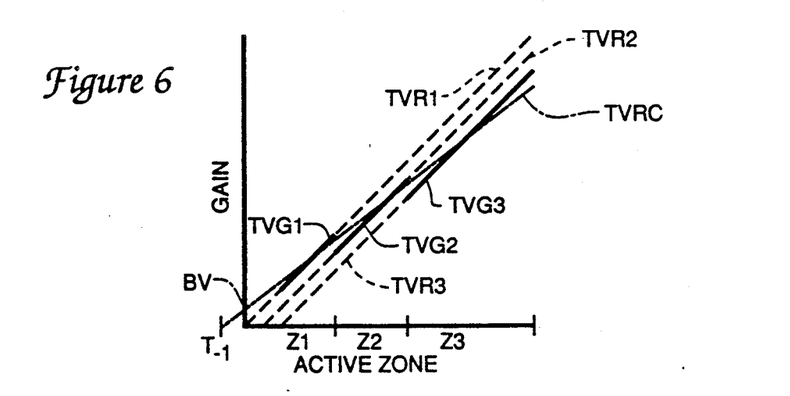
FIG. 6 is a schematic graph showing time-varying gain functions employed in the ultrasound system of FIG. 1.

The ideal time-varying gain function for zones Z1, Z2 and Z3 are respectively TVG1, TVG2 and TVG3, as shown in FIG. 6. The gain dimension is scaled in FIG. 6 in a nonlinear manner so that the gain functions can be represented as straight line segments. At the Z1 to Z2 transition, TVG2 is less than TVG1 by an amount calculated to compensate for the increased transmit power delivered to zone Z2. A similar relationship exists between TVG2 and TVG3 at the transition of zones Z2-Z3. This downward step matches the brightness of adjacent zones at their common boundary, thus minimizing brightness discontinuities at zone boundaries in the displayed ultrasound image.

A practical method of implementing the time-varying gain function is to generate three similar time-varying gain ramps TVR1, TVR2 and TRV3. TVR1 includes TVG1 so the proper gain is applied to the echoes received from zone Z1. A gain is also applied to burst BB1 echoes received from zones Z2 and Z3, resulting in some extraneous out-of-focus signals and processing. The extraneous signals will be eliminated at video buffer 334. Ramp TVR2 is similar to ramp TVR1. However, zone sequencer 302 supplies a timing signal which delays the onset of ramp TVR2 as shown in FIG. 6 so that it includes the desired time-varying gain function TVG2. TVG3 and TVR3 are similarly related.

In an alternative mode, a common ramp TVRC is applied for all zones. No onset delay signal from sequencer 302 is required. Ramp TVRC is a compromise in that it does not track any of the ideal time-varying gain functions exactly. It is initiating using either an early onset at $T-1$ or with a positive voltage bias BV. Ramp TVRC has a lesser slope than the ideal time-varying gain functions and ramps to compensate for the downward steps between successive time-varying gain functions TVG1, TVG2, and TVG3. In practice, the bias and slope of a common ramp would be varied until a satisfactory result would be obtained. Since TVRC is not stepped, a deeper zone is brighter than the adjacent shallower zone at their common boundary. However, this discontinuity in brightness is far more tolerable than a temporal discontinuity.

The amplified echo signal segments are then processed by echo processing section 332. Echo processing section 332 introduces relative delays between the echo signal segments of an echo signal set, i.e., echo signal segments resulting from a common burst. The as-delayed signals are then combined to yield a video signal. In echo processing section 332, the processing is performed digitally.

To this end, echo processing section 332 includes a bank of twenty-four analog-to-digital converters (ADCs). Prior to digitization, each echo signal is duplicated so that there are two replicas of each echo signal. One replica is digitized to yield an inphase digitized version of the echo signal. The other replica is sampled 90° out-of-phase of the first replica to yield a quadrature digitized version of the echo signal. The inphase and quadrature replicas collectively preserve phase information of the original echo signal. Each echo signal set thus yields twelve inphase digital replicas and twelve quadrature digital replicas.

The total of twenty-four digitized replicas are delivered to a band of twenty-four delay devices, which can be first-in-first-out storage devices (FIFOs). Variable delays are introduced in each replica by adjusting the input clocks of each inphase and quadrature FIFO pair. The outputs of the FIFOs are combined in a pipelined adder yielding an inphase sum signal and a quadrature sum signal. Further processing involves interpolating the summed signals using finite impulse response filters so that the inphase and quadrature components can be recombined with the proper phase to yield a video signal segment.

The recombined signal is directed into video buffer 334 which assembles sector lines. One of the functions of video buffer 334 is to gate video signal segments to remove unwanted portions. Each burst results in three sets of echoes: leading echoes that arrive before echoes from the focal zone for the burst, echoes from the focal zone, and trailing echoes that arrive after echoes from the focal zone.

Figure 5:
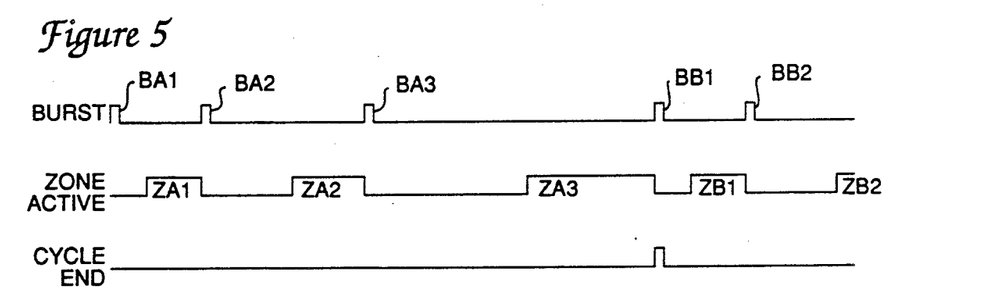
FIG. 5 is a schematic timing diagram showing the timing relationship between bursts and zone splicing in the ultrasound system of FIG. 1.

The leading and trailing echoes do not contribute to the final image. However, it is convenient to process them along with the zone echoes. The input to video buffer 334 is disabled by a false ZONE ACTIVE signal from zone sequencer 302 so that the leading echo portion of an video signal segment is discarded. The relative timings of bursts and the ZONE ACTIVE signal are represented in FIG. 5, in which ZONE ACTIVE periods ZA1, ZA2, ZA3, ZB1 and ZB2 are indexed by steering position and zone. The ZONE ACTIVE signal goes true for duration ZA1 when sequencer 302 determines sufficient time has elapsed for processed zone echoes to reach video buffer 334 so that the zone echo portion of a video signal segment is stored in video buffer 334. The ZONE ACTIVE goes false when sequencer 302 determines that all of the zone echo information from a burst has been stored so that the trailing edge portion of a video signal segment is discarded.

Once the zone echo portion of the video segment resulting from burst BA1 is stored, the ZONE ACTIVE signal remains false until the zone echo portion of the video segment resulting from burst BA2 arrives at video buffer 334. The ZONE ACTIVE signal is held true for duration ZA2 so that the leading and trailing portions of the next video signal segment are discarded. The zone echo portion of this video signal segment is appended to the zone echo portion of the preceding video echo segment. In a like manner, the zone echo portion of the video signal segment resulting from burst BA3 is appended to the zone echo portion resulting from burst BA2. Accordingly, the zone echo portions resulting from the burst cycle BA1-BA3 are spliced together in video buffer 334 to define a raster line corresponding to steering position SPA.

When a first raster line is completed, zone sequencer 302 transmits a CYCLE END signal, the timing of which is indicated in FIG. 6, which resets video buffer 334. Video buffer 334 contains parallel buffer memories which are used alternately. As the sector line corresponding to steering position SPA is transmitted from a first buffer memory to scan converter 335, a sector line corresponding to steering position SPB is assembled in the other buffer memory. If the time-varying gain functions have been suitably selected, brightness discontinuities should be minimal at zone boundaries, corresponding to splice positions on the sector lines. Otherwise, brightness discontinuities can occur, but temporal discontinuities are essentially eliminated.

Scan converter 335 converts sector lines to raster format. Monitor 336 can display about 240 raster lines during each display cycle. Each raster line corresponds to a steering position and represents as many zones as there are bursts per burst cycle. With the illustrated configuration zones Z1, Z2 and Z3 selected as described above, the display can cycle faster than 10 Hz, which is more than sufficient for real time control by an operator.

Ergonomic studies have indicated that a steering cycles rate of at least 7–11 Hz is required for "real-time" feel. In other words, the product of the number of steering positions and the time required per steering position can be no more than 90–140 milliseconds (ms). A typical steering range of 45° can require 240 steering positions for adequate angular resolution. The times between a burst and the reception of all the echoes within its target zone are about 50 microseconds ($\mu s$) for zone Z1, 100 $\mu s$ for zone Z2 and 200 $\mu s$ for zone Z3. This yields about 350 $\mu s$ per steering position or 84 ms per steering cycle. This yields a steering cycle rate between 11 and 12 Hz, which is ample for real-time operation.

If more and deeper zones are desired, the time required for each steering position is increased. Real-time feel can be sacrificed where it is not required. Otherwise, steering range and/or angular resolution can be restricted. The present invention can be fine tuned by gating each series of echo signals when the echoes from the most distant portion of the target range are received, rather than waiting for the most distant echo from the last zone; this would permit more optimal steering ranges to be achieved. Other embodiments of the present invention provide for multiplexing coded transmission, for example, using frequency multiplexing, so that the multiple wavefronts for a given steering position can be concurrent rather than successive. The time per steering position then is limited only by the time for the most distant echo to be received.

Delivered power can be controlled by adjusting transmit power, frequency and sharpness of focus. The present invention provides for embodiments in which sharpness of focus can be adjusted using various axicon focus techniques. The sharpness settings are preferably accounted for in determining transmit power. Frequency adjustments are handled similarly. Transmit power can be adjusted by controlling the number of pulse trains per burst, the number of pulses per train, pulse duration and pulse amplitude. In the default mode for ultrasound system 100, pulse duration is a function of frequency which is held constant. Transmit power can then be varied by controlled burst duration, which can be measured by the number of pulses in a train. The number of pulses per train can be varied, for example, from one to four, with trains of two or three pulses being more common than trains of one or four pulses. All of these parameters and modes can be adjusted for other applications.

The present invention applies to different phased-array transducer types. Spherical, parabolic and planar annular arrays as well as linear and two-dimensional planar arrays are provided for. These and other variations upon and modifications to the described embodiments are provided for by the present invention, the scope of which is limited only by the following claims.

What is claimed is:

1. An ultrasound system comprising:
   a transducer for converting electrical power bursts into respective acoustic wavefronts;
   burst means for generating said power bursts, said burst means being coupled to said transducer so that each of said power bursts generates a respective acoustic wavefront, each of said power bursts being characterized by a transmit power and a focal point at which the resulting wavefront converges, said focal point determining a focal depth for its burst;
   sequencer means for cycling through a referent series of n focal zone referents corresponding to a zone series of n focal zones;
   focus means for controlling said focal depths of said bursts so that said respective focal points of a burst series including n of said bursts fall respectively within said n focal zones, said focus means being coupled to said sequencer means for receiving said focal zone referents and coupled to said burst means for controlling said bursts; and
   power means for controlling said transmit power of said power bursts as a function of said focal depth, said power means being coupled to said sequencer means for receiving said focal zone referents and to said burst means for controlling said transmit power of said power bursts.

2. A system as recited in claim 1 wherein said transducer is a phased array with plural transducer elements, each of said bursts including plural concurrent pulse trains, each of said pulse trains containing at least one electrical pulse, each of said pulse trains being conveyed to a respective one of said transducer elements.

3. A system as recited in claim 2 wherein said zone series is characterized by successively increasing said focal depths.

4. A system as recited in claim 3 wherein each of said pulse bursts is characterized by a pulse amplitude which is a function of the average amplitude of all said pulses in all said trains in a said burst, said transmit power being increased by increasing said pulse amplitude with increasing said focal depth.

5. A system as recited in claim 3 wherein each of said pulse bursts is characterized by a pulse count which is a function of the average pulse count of all said pulse trains in a said burst, said transmit power being increased by increasing said pulse count with increasing said focal depth.

6. A system as recited in claim 3 wherein each of said pulse bursts is characterized by a pulse duration which is a function of the average pulse duration of all said pulses of all said pulse trains in a said burst, said transmit power being increased by increasing said pulse duration with increasing said focal depth.

7. A system as recited in claim 3 further wherein said power means includes element select means for selectively enabling and disabling said transducer elements, whereby said transmit power can be increased by increasing the number of enabled said transducer elements with increasing said focal depth.

8. A system as recited in claim 2 further comprising:
   receiver means for receiving a series of echo signal sets from said transducer, each of said echo signal sets resulting from the conversion of a received echo wavefront to electrical energy by said transducer, each said received echo wave front being produced by a respective burst so that said each echo signal set corresponds to a said burst, each said echo signal of said each echo signal set corresponding to a respective transducer element, said receiver means including:

echo signal processing means for introducing variable relative delays between said echo signals of each said echo signal set, and for combining and processing the as-delayed echo signals of a said echo signal set to yield video signal segments, each said video signal segment corresponding to a respective echo signal set;

splicing means for splicing together successive said video signal segments corresponding to said bursts of one of said burst series to yield a series of sector lines, each of said sector lines corresponding to one of said burst series; and display means for displaying said sector lines successively generated by said splicing means.

9. A system as recited in claim 8 wherein said receiver means includes time-varying gain means for applying time-varying gain functions to said echo signal sets, said of said time-varying gain functions applied to a given said echo signal set being a function of said focal depth of said burst corresponding to said echo signal set.

10. A system as recited in claim 9 wherein two of said zones have a common boundary, said time-varying gain functions being successively selected so as to minimize brightness discontinuities in an image displayed on said display means at positions corresponding to said splices between pairs of said video signal segments.

* * * * *